US008765651B2

(12) United States Patent
Hutton, III et al.

(10) Patent No.: US 8,765,651 B2
(45) Date of Patent: *Jul. 1, 2014

(54) METHOD OF CLEANSING HAIR

(75) Inventors: Howard David Hutton, III, Oregonia, OH (US); Jeffrey John Scheibel, Loveland, OH (US); David Johnathan Kitko, Cincinnati, OH (US); Jun Xu, Mason, OH (US); Charles Winston Saunders, Fairfield, OH (US); Kenneth Nathan Price, Cincinnati, OH (US); Stephanie Ann Urbin, Cincinnati, OH (US); Phillip Richard Green, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/182,919

(22) Filed: Jul. 14, 2011

(65) Prior Publication Data

US 2012/0012130 A1    Jan. 19, 2012

Related U.S. Application Data

(60) Provisional application No. 61/364,519, filed on Jul. 15, 2010.

(51) Int. Cl.
| | |
|---|---|
| *A61Q 5/02* | (2006.01) |
| *A61K 8/46* | (2006.01) |
| *B08B 3/04* | (2006.01) |
| *C11D 1/02* | (2006.01) |
| *C11D 1/12* | (2006.01) |

(52) U.S. Cl.
USPC ........... 510/127; 510/119; 510/123; 510/159; 510/426; 510/437; 510/492; 424/70.5; 424/70.24; 424/70.27

(58) Field of Classification Search
USPC ......... 510/119, 123, 127, 159, 426, 437, 492; 424/70.5, 70.24, 70.27
See application file for complete search history.

(56) References Cited

U.S. PATENT DOCUMENTS

| | | | |
|---|---|---|---|
| 4,985,466 A | 1/1991 | Deguchi | |
| 5,476,649 A | 12/1995 | Naito et al. | |
| 6,335,312 B1 * | 1/2002 | Coffindaffer et al. | 510/159 |
| 6,562,328 B2 | 5/2003 | Pereira et al. | |

(Continued)

FOREIGN PATENT DOCUMENTS

| | | |
|---|---|---|
| DE | 1944544 A1 | 3/2001 |
| GB | 2185488 A | 7/1987 |

(Continued)

OTHER PUBLICATIONS

PCT International Search Report and Written Opinion dated Mar. 25, 2013.

*Primary Examiner* — Brian P Mruk
(74) *Attorney, Agent, or Firm* — Angela K. Haughey

(57) ABSTRACT

Method of cleansing hair comprising: (a) applying a composition to the hair; (b) dissolving and lathering the composition using a water-based solvent; (c) rinsing the hair with a water-based solvent; wherein during the rinsing a total of about 100 gram to about 300 gram of water-based solvent per gram of hair (dry weight) is employed; wherein the composition comprises from about 3 wt % to about 35 wt % of a mixture of at least two compounds of Formula I.

14 Claims, 1 Drawing Sheet

(56) References Cited

U.S. PATENT DOCUMENTS

| | | |
|---|---|---|
| 7,422,756 B2 | 9/2008 | Haadem |
| 8,147,813 B2 | 4/2012 | Beauquey et al. |
| 8,338,348 B2 | 12/2012 | Anim-Danso et al. |
| 2003/0202954 A1* | 10/2003 | Pereira et al. ............. 424/70.28 |
| 2004/0076654 A1 | 4/2004 | Vinson et al. |
| 2005/0020468 A1 | 1/2005 | Frantz et al. |
| 2009/0221463 A1* | 9/2009 | Kitko et al. .................. 510/120 |
| 2012/0012130 A1 | 1/2012 | Hutton, III et al. |
| 2012/0014900 A1 | 1/2012 | Carter et al. |
| 2012/0014901 A1 | 1/2012 | Sunkel et al. |

FOREIGN PATENT DOCUMENTS

| | | |
|---|---|---|
| JP | 2000-344697 | 12/2000 |
| JP | 2001302465 | 10/2001 |
| JP | 2003055699 | 2/2003 |
| WO | 99/18929 A1 | 4/1999 |

* cited by examiner

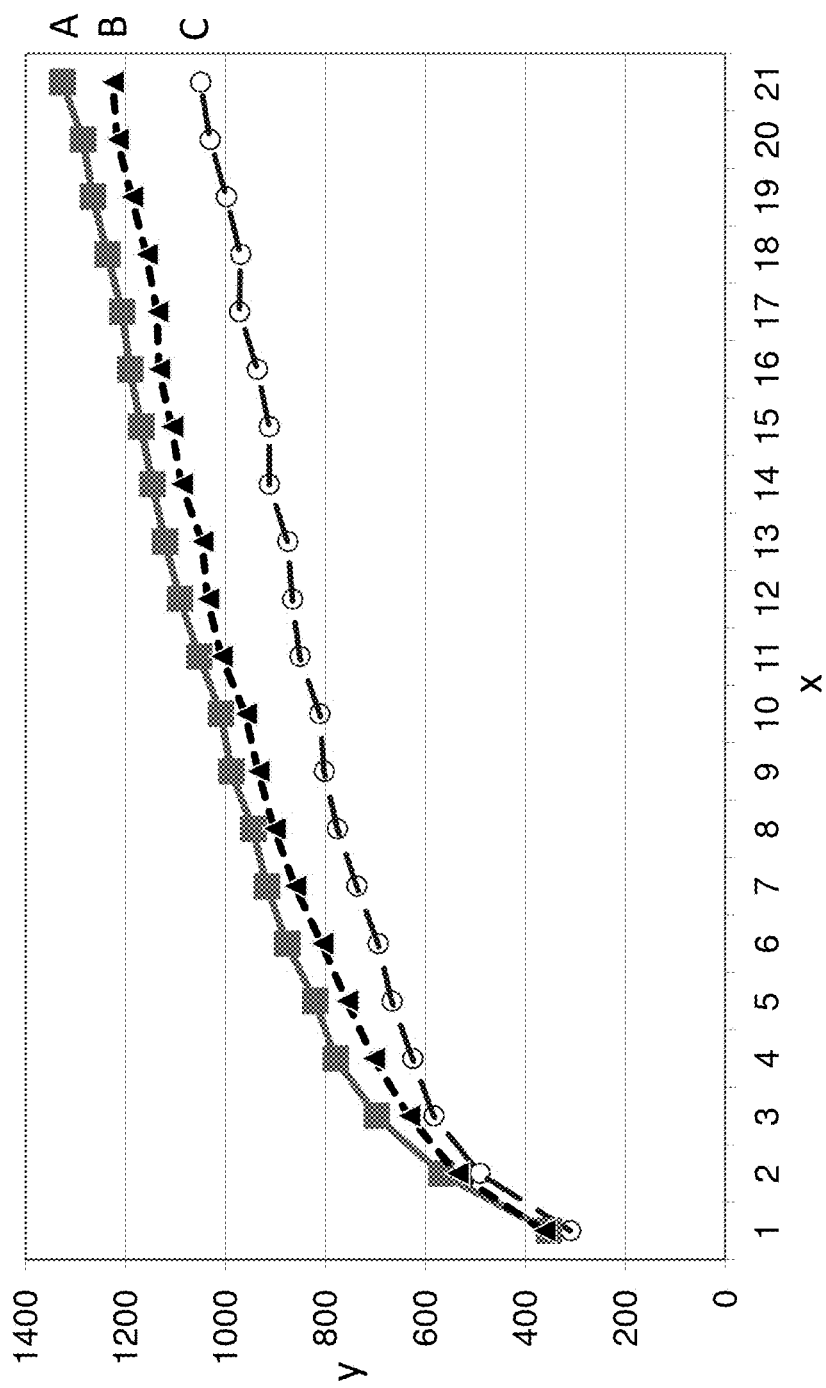

METHOD OF CLEANSING HAIR

CROSS REFERENCE TO RELATED APPLICATION

This application claims the benefit of U.S. Provisional Application No. 61/364,519, filed Jul. 15, 2010.

FIELD OF THE INVENTION

Method of cleansing hair comprising: (a) applying a composition to the hair; (b) dissolving and lathering the composition using a water-based solvent; (c) rinsing the hair with a water-based solvent; wherein during the rinsing a total of about 100 gram to about 300 gram of water-based solvent per gram of hair (dry weight) is employed; wherein the composition comprises from about 3 wt % to about 35 wt % of a mixture of at least two compounds of Formula I.

BACKGROUND OF THE INVENTION

Cleansing compositions specifically tailored for hair are routinely utilised, typically, on a daily basis. When cleansing human hair, a cleansing composition, or shampoo, is typically dispensed from the packaging and applied to pre-wetted hair. The cleansing composition is rubbed into the hair using the hands and distributed to all hairs that require cleansing. Through dissolving in water and the rubbing action of the hands, a lather is formed. When lather is formed, due to the formation of air bubbles, the volume of the cleansing composition increases and so it can be spread across the whole head of hair more easily. Lather is an important indicator to consumers that cleansing is occurring. After allowing the cleansing composition to cleanse the hair, which typically lasts from a few sec to a number of minutes, the composition is rinsed from the hair using water.

There is a correlation between the surfactant parameters that drive good cleansing (e.g. packing at interfaces, ability to aggregate) and the ability to form lather. There is a need for a surfactant that will go to the air-water and soil-water interface very quickly, which comes from the packing of the surfactant molecules e.g. at the interfaces. Branched surfactants go to these interfaces quickly and efficiently because they are in monomeric form as result of their more loose packing (due to branches) and hence are not part of a big aggregate, which needs to get broken down in order to reach the interfaces. However, tight packing correlates with good lather quality. Critical micelle concentration (CMC) correlates with speed of lathering because micelles are less tightly packed, but this also correlates with lower lather quality. A downside of having tightly packed micelles (low CMC), which need to be broken down, is slow lather and therefore slower cleansing.

As the human population increases and societies become more highly developed, which typically results in increased demand, the availability and costs of basic resources such as water increase. Furthermore, in some parts of the world, for example those close to the equator, water is always in relatively short supply. There is a need, therefore, for providing methods to cleanse hair that can be used when water is in short supply or is relatively unaffordable.

In order to use less water for cleansing hair, the composition should be able to dissolve in less water than required for conventional compositions. Furthermore, it should form a lather when less water is utilised. Moreover, less water should be able to be used in order to rinse the composition from the hair. In modern times, there is a desire for daily household tasks such as cleansing to be made as fast as possible. In the context of a composition for the hair, this requires faster dissolution (dissolving) time, faster lather formation, and/or faster rinsing. Finally, there is a need to find cleansing actives which can be derived from natural and renewable sources.

The use of branched compounds in cleansing compositions are already known e.g. WO99/18929; WO2005/009385; U.S. Pat. No. 6,150,312; WO2009/090617; WO2009/053931. None of the existing art provides all of the advantages and benefits of the present invention.

SUMMARY OF THE INVENTION

In a first aspect, the present invention relates to a method of cleansing hair comprising:
(a) applying a composition to the hair;
(b) dissolving and lathering the composition using a water-based solvent;
(c) rinsing the hair with a water-based solvent;
wherein during the rinsing a total of about 100 gram to about 300 gram of water-based solvent per gram of hair (dry weight) is employed;
wherein the composition comprises from about 3 wt % to about 35 wt % of a mixture of at least two compounds of Formula I:

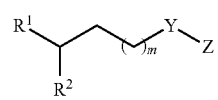

wherein $R^1$ is hydrogen, methyl, or ethyl; $R^2$ is $(C_1-C_n)$alkyl or $(C_1-C_n)$alkenyl having 0, 1, 2, or 3 $(C_1-C_3)$alkyl branches, wherein branching occurs on carbon atoms that are within 40% of the nonfunctionalized terminus of the carbon backbone; m is 5-37 and n is 1-33, wherein m+n is 6-38; Y is null, or $W_p$; W is selected from the group consisting of ethylenoxy, propylenoxy, butylenoxy, and mixtures thereof; p is 1 to 30; Z is a hydrophilic moiety selected from the group consisting of hydroxy, carboxylate, sulfate, disulfate, sulfonate, disulfonate, glycerol ester sulfonate, amine, monoalkylamine, dialkylamine, amine oxide, a polyhydroxy moiety, a phosphate ester, glycerol sulfonate, polygluconate, a polyphosphate ester, phosphonate, sulfosuccinate, sulfosuccaminate, glucamide, taurinate, sarcosinate, glycinate, isethionate, dialkanolamide, monoalkanolamide, monoalkanolamide sulfate, diglycolamide, diglycolamide sulfate, a glycerol ester, a glycerol ester sulfate, a glycerol ether, a glycerol ether sulfate, a polyglycerol ether, a polyglycerol ether sulfate, sorbitan ester, an alkylpolyglucoside, urea, ammonioalkanesulfonate, amidopropyl betaine, an allylated quat, an alkyated/polyhydroxyalkylated quat, an alkylated quat, an alkylated/polyhydroxylated oxypropyl quat, a glycerol ester quat, a glycol amine quat, imidazoline, alken-2-yl-succinate, a sulfonated alkyl ester, and a sulfonated fatty acid;
wherein with respect to at least one of the compounds: when $R^1$ is H, then $R^2$ has 1, 2, or 3 $(C_1-C_3)$alkyl branches and when $R^1$ is methyl or ethyl then $R^2$ has 0, 1, or 2 $(C_1-C_3)$alkyl branches.

In a second aspect, the present invention relates to a composition for cleansing hair wherein the composition dissolves in a water-based solvent with a dissolution time of from about 0.1 sec to about 300 sec, wherein the composition comprises from about 3 wt % to about 35 wt % of a mixture of at least two compounds of Formula I as described above.

In a third aspect, the present invention relates to the use of a composition for cleansing hair wherein the composition dissolves in a water-based solvent with a dissolution time of from about 0.1 sec to about 300 sec, wherein the composition comprises from about 3 wt % to about 35 wt % of a mixture of at least two compounds of Formula I as described above.

BRIEF DESCRIPTION OF THE DRAWINGS

FIG. 1 shows a graph of number of rinsing strokes versus friction for three different compositions. The x-axis is number of strokes of the comb/brush and the y-axis is friction (in grams of force). Compositions A and B are pursuant to the present invention. Composition C is not pursuant to the present invention.

DETAILED DESCRIPTION OF THE INVENTION

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated.

All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Herein, "comprising" means that other steps and other ingredients which do not affect the end result can be added. This term encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

As used herein, "near terminal-branched" fatty acids, fatty alcohols, and derivatives of fatty acids and alcohols (i.e., "near-terminal branched compounds") contain 1, 2, or 3 ($C_1$-$C_3$)alkyl branches on a carbon atom within 40% of the non-functionalized end of the longest chain. The functionalized end of the near-terminal branched fatty acids, fatty alcohols, and derivatives of fatty acids and alcohols is that which contains the acid, alcohol, or derivative moieties. The non-functionalized carbon at the end of carbon backbone is referred to as the 'omega' position. For example, near-terminal branched compounds that are 10 carbon atoms in length can have branching up to the omega-3 position, while near-terminal branched compound s that are 30 carbon atoms in length can have branching up to the omega-11 position. The near-terminal branched compounds herein typically have branching at the omega-1, omega-2, omega-3, omega-4, omega-5, and/or omega-6 positions of the compound, or at the omega-1, omega-2, and/or omega-3 positions, or at the omega-1 and/or omega-2 positions.

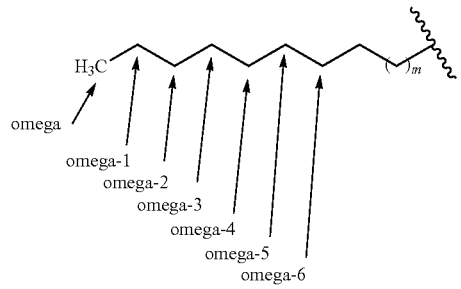

Near terminal-branched compounds with branching at the omega-1 position are referred to as "iso". Near terminal-branched compounds with branching at the omega-2 position are referred to as "anteiso". For example, a compound with 10 carbon atoms in its carbon backbone with a methyl branch at the omega-1 position: the branch is within 40% of the non-functionalized end of the carbon chain (e.g., 2/10× 100%=20%) and is referred to as near terminal-branched. In contrast, a compound with 10 carbon atoms in its carbon backbone and methyl branch at the omega-4 position—the branch is not within 40% of the non-functionalized end of the carbon chain (e.g., 5/10×100%=50%) and so is not referred to as "near terminal-branched."

As used herein, the term "alkyl" refers to straight chained and branched saturated hydrocarbon groups. As used herein, the term "alkenyl" is defined identically as "alkyl" except for containing a carbon-carbon double bond, e.g., ethenyl, propenyl, and butenyl.

As used herein, "linear" fatty acids, fatty alcohols, and derivatives of fatty acids and alcohols (i.e., "linear compounds") are free of branches on the carbon chain.

As used herein, "mid-chain" branched fatty acids, fatty alcohols, and derivatives of fatty acids and alcohols (i.e., "mid-chain branched compounds") contain alkyl branches on a carbon atom that is between about 40% to about 60% of the non-functionalized end of the carbon backbone. For example, a mid-chain branched compound that is 12 carbon atoms in length can have branching on the omega-5 and/or omega-6 position. A mid-chain branched compound that is 30 carbon atoms in length can have branching on the omega-12 to the omega-17 position.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Carbon backbone", as used herein, means the carbon backbone in the compound.

"Derivatives," as used herein, includes but is not limited to, amide, ether, ester, amino, carboxyl, acetyl, and/or alcohol derivatives of a given compound.

The cleansing compositions as described herein provide excellent performance benefits. These benefits include: excellent, fast dissolution (dissolving) and require less water to dissolve than conventional cleansing compositions; fast lather formation resulting in a lower lathering time; fast and complete rinsing resulting in a shorter rinsing time. Furthermore, the compositions are stable at low temperatures and tolerate hard water conditions.

Without being bound by theory, the inventors believe that branched compounds pack less efficiently compared with linear compounds. The packing efficiency depends on the placement of the branch in the compound and size of the branch. Efficient packing correlates with good lathering and cleansing, but over efficient packing leads to crystallinity and consequently less desired dissolution, less desired rinsing and less desired lather kinetics. The inventors have furthermore discovered that the degree of packing can be adjusted by optimizing the ratio of branched compound to linear compound and adjusted also by the branch placement in the branched compound. The presence of a linear compound in the composition provides optimisation of the benefits of the branched compound.

The first aspect relates to a method of cleansing hair comprising applying a composition to the hair. The method also comprises dissolving and lathering the composition using a water-based solvent. In an embodiment, the water-based solvent is at least about 50 wt %, or at least about 60 wt %, or at least about 70 wt %, or at least about 80 wt %, or at least about 90 wt % water.

In an embodiment, the dissolving comprises a dissolution time of from about 0.1 sec to about 300 sec, or about 50 sec to about 250 sec, or about 100 sec to about 200 sec, or about 120 sec to about 180 sec, or about 150 sec to about 160 sec. "Dissolution time", as used herein, is the time it takes for the composition to be completely dispersed in the water. Dissolution time can be measured by measuring electrical conductance changes in a water solution. As the composition dissolves the conductance increases due to the presence of more ions in solution. When the composition is completely dissolved and in solution, the conductance value levels out to a final and constant number. Consequently, measurement of the dissolution time starts when you add composition to water and stops when the conductance reaches its final value. This is a technical measure for dissolution time and is correlated to the actual consumer dissolution time. However, the different consumers add different amounts of energy (e.g. by rubbing their hands together) into the composition/solvent, but improved technical dissolution time leads to improved consumer use dissolution time.

In an embodiment, the lathering comprises a lathering time of from about 0.1 sec to about 80 sec, or from about 2 sec to about 60 sec, or about 5 sec to about 50 sec, or from about 10 sec to about 30 sec, in order for a composition comprising 0.19 gram total surfactant to reach 200 mL total volume of lather. "Lathering time", as used herein, is how quickly the lather volume goes up with use. Lathering time can be measured by use of a machine that generates lather mechanically. If a composition shows an advantage in producing lather more quickly (time of mechanical action) it correlates with it being easier to generate lather during consumer use. Lather volume over time can measured and comparisons made for a plurality of different compositions measured simultaneously. The difference in lather volume between two different compositions can be measured a specific time point e.g. after 20 sec, alternatively the time taken to reach a specific lather volume can be measured.

The method also comprises rinsing the hair with a water-based solvent. In an embodiment, during the rinsing a total of about 120 gram to about 270 gram, or 140 gram to about 250 gram, or 150 gram to about 240 gram, or about 160 gram to about 230 gram, or about 170 gram to about 210 gram, or 180 gram to about 200 gram of water-based solvent per gram of hair (dry weight) is employed.

The composition comprises from about 3 wt % to about 35 wt % of a mixture of at least two compounds of Formula I as described above. In an embodiment, the composition comprises from about 4 wt % to about 34 wt %, or from about 5 wt % to about 30 wt %, or from about 10 wt % to about 28 wt %, or from about 20 wt % to about 25 wt % of a mixture of at least two compounds of Formula I as described above.

In an embodiment, the composition comprises at least one linear compound according to Formula I and at least one branched compound according to Formula I. In the linear compound according to Formula I: $R^1$ is H; and $R^2$ is $(C_1-C_n)$ alkyl or $(C_1-C_n)$alkenyl and is free of branches on the carbon chain.

In an embodiment, the weight ratio of linear compound to branched compound (linear:branched) is from about 10:1 to about 1:2, or from about 5:1 to about 1:1, or from about 4.5:1 to about 1.75:1; or from about 3.5:1 to about 2.5:1.

In an embodiment, the branched compound is selected from the group consisting of: near-terminal branched compounds; mid-chain branched compounds; and mixtures thereof. In an embodiment, the branched compound is a near-terminal branched compound. In an embodiment, the branched compound comprises at least one branch located at a position selected from the group consisting of: omega-1, omega-2, omega-3, omega-4, omega-5, and omega-6; or omega-1, omega-2, and omega-3; or omega-1 and omega-2. In an embodiment, the branched compound comprises only one branch, wherein the branch is located at a position selected from the group consisting of: omega-1, omega-2, and omega-3; or omega-1 and omega-2. The composition may be substantially free of any branched compound that is neither a near-terminal branched compound nor mid-chain branched compound. In an embodiment, the composition is substantially free of a mid-chain branched compound.

In an embodiment, the branched compound comprises a branch wherein the branch is selected from the group consisting of methyl and ethyl branches, or wherein the branch is a methyl branch. The branch may comprise carbon and hydrogen atoms only. In an embodiment, the branched compound is selected from the group consisting of: 10-methyldodecylsulfate sodium or ammonium salt, 11-methyldodecylsulfate sodium or ammonium salt, 10-methyldodecylsulfate-ethoxylated sodium or ammonium salt, 11-methyldodecylsulfate-1-ethoxylated sodium or ammonium salt, and mixtures thereof. Such branched compounds can be synthesised using the below synthesis information and/or purchased from Aldrich and other specialty chemical producers.

In an embodiment, the linear compound is the salt of an anionic surfactant comprising 12 to 14 carbon atoms. The linear compound may be selected from the group consisting of: sodium lauryl sulfate, sodium laureth sulfate, sodium tridecyl sulfate, sodium trideceth sulfate, sodium myristyl sulfate, sodium myreth sulfate, and mixtures thereof.

The composition may further comprise a co-surfactant. In an embodiment, the co-surfactant is an anionic co-surfactant, which may be present in amount of from about 0.01% to about 20%, or from about 0.1% to about 5%, by total weight of the composition. The anionic co-surfactants may be selected from the group consisting of: ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and mixtures thereof. In an embodiment, the anionic co-surfactant is sodium lauryl sulfate or sodium laureth sulfate. In an embodiment, the anionic co-surfactant is selected from the group consisting of CAPB (cocoamidopropyl betaine), Cocobetaine (CocoB), sodium lauroylamphoacetate (NaLAA), laurylhydroxysultaine (LHS), cocomonoethanol amide (CMEA), and mixtures thereof.

The composition may comprise a high melting point fatty compound. The high melting point fatty compound useful herein has a melting point of 25° C. or higher, and is selected from the group consisting of a fatty alcohol, fatty acid, fatty alcohol derivative, fatty acid derivative, and mixtures thereof. Non-limiting examples of the high melting point compounds are found in International Cosmetic Ingredient Dictionary, Fifth Edition, 1993, and CTFA Cosmetic Ingredient Handbook, Second Edition, 1992. The composition may comprise from about 0.1% to about 40%, or from about 1% to about 30%, or from about 1.5% to about 16%, or from about 1.5% to about 8% of a high melting point fatty compound, by total weight of the composition, in view of providing improved conditioning benefits such as slippery feel during the application to wet hair, softness and moisturized feel on dry hair. In an embodiment, fatty alcohol is selected from the group consisting of: cetyl alcohol, stearyl alcohol, behenyl alcohol, and mixtures thereof.

The composition may comprise a cationic polymer. The composition may comprise from about 0.05% to about 3%, or from about 0.075% to about 2.0%, or from about 0.1% to about 1.0% of cationic polymer, by total weight of the composition. The cationic polymers may have cationic charge densities of from about 0.5 meq/gram to about 7 meq/gram, or from about 0.9 meq/gram to about 5 meq/gram, or from about 1.2 meq/gram to about 4 meq/gram, at the pH of intended use of the composition, which pH will generally range from about pH 3 to about pH 9, or between about pH 4 and about pH 8. Herein, "cationic charge density" of a polymer refers to the ratio of the number of positive charges on the polymer to the weight average molecular weight of the polymer. The weight average molecular weight of the cationic polymer may be between about 10,000 and 10 million, or between about 50,000 and about 5 million, or between about 100,000 and about 3 million.

Suitable cationic polymers may comprise cationic nitrogen-containing moieties such as quaternary ammonium or cationic protonated amino moieties. The counterion may be selected from the group consisting of halides (e.g., chloride, fluoride, bromide, iodide), sulfate, methylsulfate, and combinations thereof. The cationic polymer may be selected from the group consisting of polysaccharide polymers, cationic guar gum derivatives, quaternary nitrogen-containing cellulose ethers, synthetic polymers, copolymers of etherified cellulose, guar and starch, and combinations thereof. The cationic polymer should be either soluble in the composition or soluble in a complex coacervate phase in the composition formed by the cationic polymer and a anionic, amphoteric and/or zwitterionic surfactant. Complex coacervates of the cationic polymer can also be formed with other charged materials in the composition.

In an embodiment, the cationic polymer is a cationic surfactant. The cationic surfactant may be selected from the group consisting of: behenyl trimethyl ammonium chloride, methyl sulfate or ethyl sulfate, and stearyl trimethyl ammonium chloride, methyl sulfate or ethyl sulfate. It is believed that a longer alkyl group provides improved smoothness and soft feeling on wet and dry hair, compared to cationic surfactants with a shorter alkyl group. It is also believed that such cationic surfactants can provide reduced irritation, compared to those having a shorter alkyl group.

In an embodiment, the cationic surfactant is a tertiary amido amine having an alkyl group of from about 12 to about 22 carbons. The tertiary amido amine may be selected from the group consisting of stearamidopropyldimethyl-, stearamidopropyldiethyl-, stearamidoethyldiethyl-, stearamidoethyldimethyl-, palmitamidopropyldimethyl-, palmitamidopropyldiethyl-, palmitamidoethyldiethyl-, palmitamidoethyldimethyl-, behenamidopropyldimethyl-, behenamidopropyldiethyl-, behenamidoethyldiethyl-, behenamidoethyldimethyl-, arachidamidopropyldimethyl-, arachidamidopropyldiethyl-, arachidamidoethyldiethyl-, and arachidamidoethyldimethyl-amine, diethylaminoethylstearamide, and mixtures thereof.

The cationic surfactant may be a di-long alkyl quaternized ammonium salt selected from the group consisting of: dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

The composition may comprise a conditioning agent. The conditioning agent may comprise a water insoluble, water dispersible, non-volatile, liquid that forms emulsified, liquid particles. The conditioning agent may be a silicone (e.g., silicone oil, cationic silicone, silicone gum, high refractive silicone, and silicone resin), a organic conditioning oil (e.g., hydrocarbon oils, polyolefins, and fatty esters), or combinations thereof, or those conditioning agents which otherwise form liquid, dispersed particles in the aqueous surfactant matrix herein. The concentration of the silicone conditioning agent may be from about 0.01% to about 10%, or from about 0.1% to about 5%, by total weight of the composition. Suitable silicone conditioning agents, and optional suspending agents for the silicone, are described in U.S. Pat. No. 5,104, 646. In an embodiment, the composition comprises a silicone gum selected from the group consisting of: polydimethylsiloxane, (polydimethylsiloxane) (methylvinylsiloxane) copolymer, poly(dimethylsiloxane) (diphenylsiloxane) (methylvinylsiloxane) copolymer and mixtures thereof.

In an embodiment, the composition comprises a terminal aminosilicone. The terminal aminosilicone may conform to Formula III:

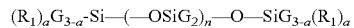

$$(R_1)_a G_{3-a}\text{-Si}-(-\text{OSiG}_2)_n-\text{O}-\text{SiG}_{3-a}(R_1)_a \qquad \text{III}$$

wherein G is hydrogen, phenyl, hydroxy, or $C_1$-$C_8$ alkyl, preferably methyl; a is an integer having a value from 1 to 3, preferably 1; b is 0, 1 or 2, preferably 1; n is a number from 0 to 1,999; $R_1$ is a monovalent radical conforming to the general formula $CqH_{2q}L$, wherein q is an integer having a value from 2 to 8 and L is selected from the following groups: —N($R_2$) $CH_2$—$CH_2$—N($R_2$)$_2$; —N($R_2$)$_2$; —N($R_2$)$_3$A$^-$; —N($R_2$) $CH_2$—$CH_2$—NR$_2$H$_2$A$^-$; wherein $R_2$ is hydrogen, phenyl, benzyl, or a saturated hydrocarbon radical, preferably an alkyl radical from about $C_1$ to about $C_{20}$; A$^-$ is a halide ion. In an embodiment, the terminal aminosilicone conforms to Formula III as described above, wherein G is methyl; a 1; b is 1; n is a number from 200 to 1000; $R_1$ is a monovalent radical conforming to the general formula $C_qH_{2q}L$, wherein q is an integer having a value from 2 to 8 and L is selected from the following groups: —N(R$_2$)CH$_2$—CH$_2$—N(R$_2$)$_2$; —N(R$_2$)$_2$; —N(R$_2$)$_3$A$^-$; —N(R$_2$)CH$_2$—CH$_2$—NR$_2$H$_2$A$^-$; wherein R$_2$ is an alkyl radical from about C$_1$ to about C$_{20}$; A$^-$ is a halide ion.

The composition may also comprise an anti-dandruff active. The anti-dandruff active may be selected from the group selected from the group consisting of: antimicrobial actives, pyridinethione salts, azoles, selenium sulfide, particulate sulfur, keratolytic acid, salicylic acid, octopirox (piroctone olamine), coal tar, and combinations thereof. The composition may comprise zinc pyridinethione (ZPT). Pyridinethione anti-dandruff agents are described, for example, in U.S. Pat. No. 2,809,971. The concentration anti-dandruff active may be from about 0.01 wt % to about 5 wt %, or from about 0.1 wt % to about 3 wt %, or from about 0.1 wt % to about 2 wt %, by total weight of the composition.

The composition may comprise a humectant. The humectants may be selected from the group consisting of polyhydric alcohols, water soluble alkoxylated nonionic polymers, and mixtures thereof. The humectants, when used herein, are preferably used at levels of from about 0.1% to about 20%, more preferably from about 0.5% to about 5% by total weight of the composition.

The composition may further comprise a suspending agent at concentrations effective for suspending water-insoluble material in dispersed form in the composition or for modifying the viscosity of the composition. The concentration of the suspending agent may range from about 0.1% to about 10%, or from about 0.3% to about 5.0%, by total weight of the composition. The suspending agent may be an anionic polymer and/or a non-ionic polymer (e.g., vinyl polymers, acyl derivatives, long chain amine oxides, and mixtures thereof, alkanol amides of fatty acids, long chain esters of long chain alkanol amides, glyceryl esters, primary amines having a fatty alkyl moiety having at least about 16 carbon atoms, secondary amines having two fatty alkyl moieties each having at least about 12 carbon atoms). Examples of suspending agents are described in U.S. Pat. No. 4,741,855.

The composition may be in the form of a pourable liquid (pourable when under ambient conditions). Such compositions will therefore typically comprise a cosmetically acceptable aqueous carrier, which is present at a level of from about 20% to about 95%, or from about 60% to about 85%. In an embodiment the composition further comprises a cosmetically acceptable aqueous carrier and is in the form of a pourable liquid. The cosmetically acceptable aqueous carrier may be selected from the group consisting of water and water solutions of lower alkyl alcohols and polyhydric alcohols. The lower alkyl alcohols may be monohydric alcohols having 1 to 6 carbons. In an embodiment, the lower alkyl alcohols are ethanol and isopropanol. The polyhydric alcohols may be propylene glycol, hexylene glycol, glycerin, and propane diol.

The above cationic surfactants, together with high melting point fatty compounds and an aqueous carrier, may form a gel matrix in the composition. The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, or from about 1:1 to about 1:10, or from about 1:1 to about 1:6. The presence of a gel network or gel matrix can be can be measured by various test methods including SAXS and DSC (Differential Scanning Calorimetry) analytical test methods.

The composition may further comprise: water soluble vitamins and their derivatives, water soluble amino acids and their salts and/or derivatives, viscosity modifiers, dyes, non-volatile solvents or diluents (water soluble and insoluble), pearlescent aids, foam boosters, additional surfactants or nonionic co-surfactants, pediculocides, pH adjusting agents, perfumes, preservatives, chelants, proteins, skin active agents, sunscreens, UV absorbers, vitamins, niacinamide, caffeine and minoxidil. The composition may comprise from about 0% to about 5% vitamins and amino acids, by total weight of the composition. The composition may also comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C.I. Names. The composition may comprise from about 0% to about 5% pigment materials. The composition may comprise from about 0% to about 5% antimicrobial agents. The composition may have a pH of from about 6 to about 10, or from about 7 to about 10, or from about 7 to about 9.

In an embodiment, the composition is substantially free of compounds that, during the lathering, slow migration of the surfactant to the air-water and/or soil-water interface. In an embodiment, the composition comprises less than about 0.5 wt %, or is substantially free of, polyacrylate associative thickeners and trihydroxystearin polymeric thickeners. Examples of polyacrylate associative thickeners include those with the trade name Carbomer. Thixcin® is an example of a trihydroxystearin polymeric thickener.

The first aspect may further comprise providing and applying to hair a hair care and/or hair styling composition. Additionally or alternatively it may comprise providing an implement for applying styling effects to the hair.

The second aspect of the present invention relates to a composition for cleansing hair, wherein the composition comprises from about 3 wt % to about 35 wt % of a mixture of at least two compounds of Formula I as described above. In an embodiment, the composition dissolves in a water-based solvent with a dissolution time of from about 0.1 sec to about 300 sec. In an embodiment, the composition comprises at least one linear compound according to Formula I and at least one branched compound according to Formula I. In an embodiment, the branched compound is selected from the group consisting of: 10-methyldodecylsulfate sodium or ammonium salt, 11-methyldodecylsulfate sodium or ammonium salt, 10-methyldodecylsulfate-ethoxylated sodium or ammonium salt, 11-methyldodecylsulfate-1-ethoxylated sodium or ammonium salt, and mixtures thereof.

Various embodiments as disclosed above for the first embodiment in relation to the composition are equally relevant to the composition of the second embodiment.

The third aspect of the present invention relates to the use of a composition for cleansing hair wherein the composition dissolves in a water-based solvent with a dissolution time of from about 0.1 sec to about 300 sec, wherein the composition comprises from about 3 wt % to about 35 wt % of a mixture of at least two compounds of Formula I as described above.

An embodiment relates to the use of a composition for cleansing hair wherein the composition dissolves in a water-based solvent with a dissolution time of from about 120 sec to about 180 sec, wherein the composition comprises from about 3 wt % to about 35 wt % of the composition comprises at least one linear compound according to Formula I and at least one branched compound according to Formula I, wherein the branched compound is selected from the group consisting of: 10-methyldodecylsulfate sodium or ammonium salt, 11-methyldodecylsulfate sodium or ammonium salt, 10-methyldodecylsulfate-ethoxylated sodium or ammonium salt, 11-methyldodecylsulfate-1-ethoxylated sodium or ammonium salt, and mixtures thereof; and wherein the weight ratio of linear compound to branched compound (linear:branched) is from about 4.5:1 to about 1.75:1.

Various embodiments as disclosed above for the first embodiment in relation to the composition are equally relevant to the use of the composition according to the third embodiment.

Synthesis Mechanism

The branched compounds may be synthesized by metathesis. Useful mechanisms are also discussed in Suguro and Mori (1979), *Agric. Biol. Chem.*, 43 (4), 869; Yuasa and Tsuruta (2004), *Flavour Fragr. J.*, 19, 199. Furthermore, production via genetically engineered bacteria is described in US2010/0105955; US2010/0105963; WO2007/136752; WO2008/119082; WO2009/111672; and U.S. 61/289,039.

Metathesis of Glyceryl Trioleate with 3-Methyl-1-Hexene, 4-Methyl-1-Hexene and 4-Methyl-1-Pentene to Prepare Near Terminal Branched Alcohols:

Reactants and subsequent products thereof can be derived from the oils: trioleate (shown in Scheme 1), soybean (hydrogenated), rapeseed, canola, palm, palm kernel, coconut, jatropha, high erucic rapeseed, cottonseed, tallow, yellow grease, corn, sunflower, babasu, and mixtures thereof. The olefin used in the metathesis reaction can be a single branched olefin, a mixture of branched olefins or a mixture of branched olefins with other nonreactive impurities such as aromatic alkyls, paraffins, branched paraffins and cycloalkanes.

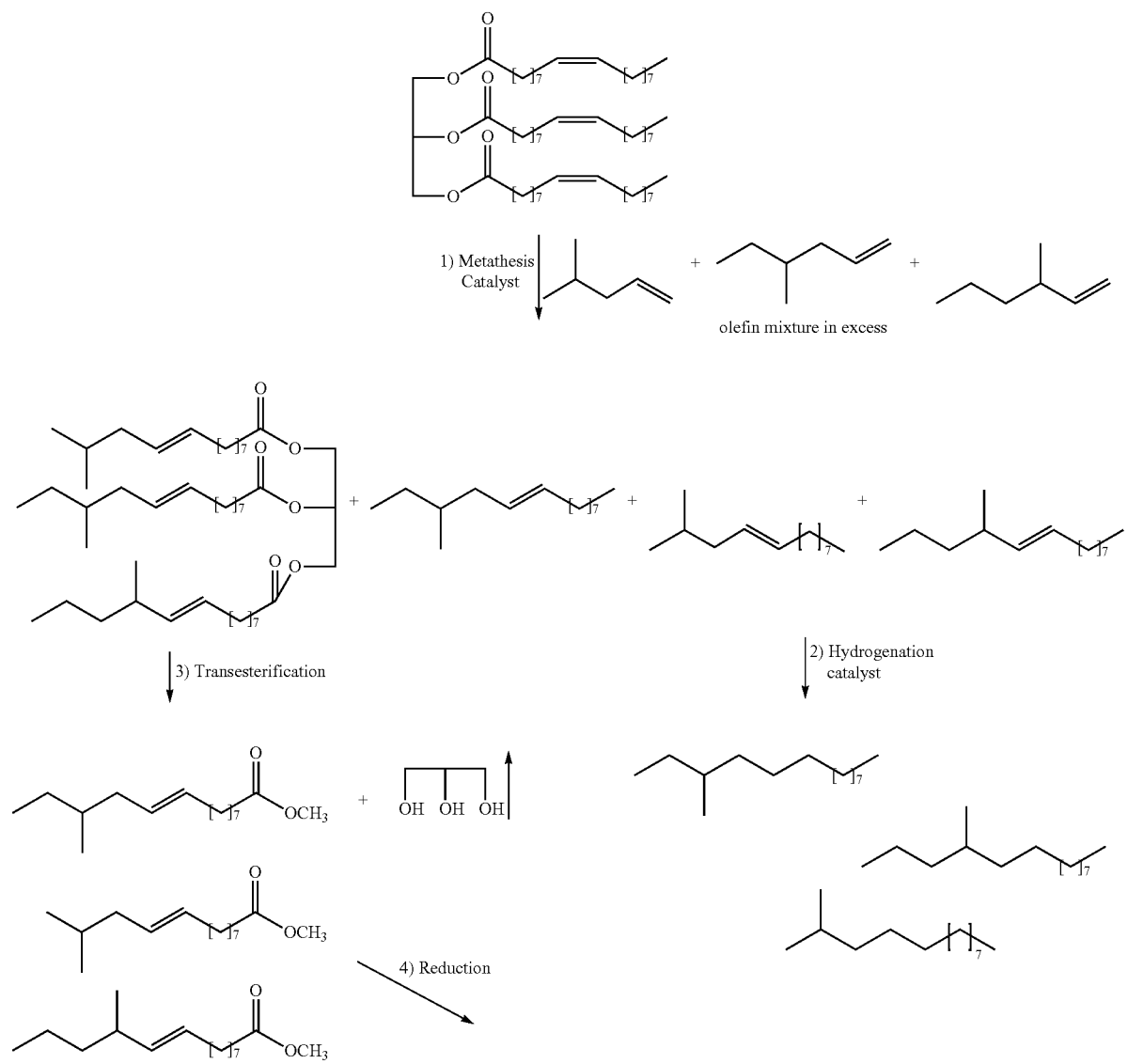

Scheme 1.

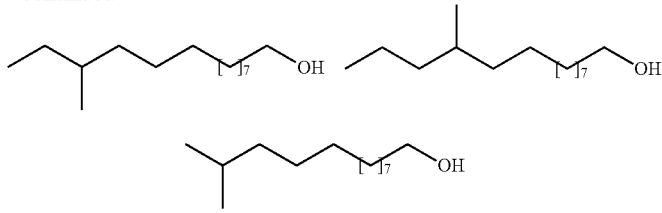

I.A. Synthesis of Mixture of Near Terminal-Branched Alcohols:

About 8.854 g (0.010 mol) of glyceryl trioleate (Sigma catalog #T7140) and 25 mL of hexane are placed in a 316 stainless steel stirred pressure vessel. Solvent and gylceryl trioleate are predried over 4A molecular sieves prior to introduction to vessel. About 0.0006 mol of tungsten hexachloride and 0.0006 mol of tetramethyl tin is added to the vessel. The reactor is sealed, stirred, and purged several times with $N_2$. About 0.030 mol of a blend of 3-methyl-1-hexene, 4-methyl-1-hexene and 4-methyl-1-pentene is added to the vessel under $N_2$. The stirred mixture is heated to 220° C. under 100 psig $N_2$ and maintained at this temperature for several hours. The reactor is cooled and the product removed. The reaction mixture is quenched with 2-3 mL of concentrated ammonium hydroxide and extracted with additional 10 mL hexane. The hexane and any volatile olefins remaining are stripped on a rotary evaporator. The remaining product is subjected to fractional distillation to remove the remaining non volatile olefin mixture. This branched olefin mixture containing mainly a mixture of 11-methyl-9-tetradecene, 12-methyl-9-tridecene and 12-methyl-9-tetradecene is hydrogenated under standard reaction conditions to provide a high quality semi-biodiesel fuel with branching. The bottom of the flask from distillation contains mainly the new branched triglyceride mixture. This new triglyceride mixture is subjected to standard transesterification conditions in the presence of methanol and a catalytic amount of sodium hydroxide or sodium methoxide in methanol. The mixture phase separates into glycerine (bottom phase) and a mixture of methyl esters (top phase) consisting mainly of 12-methyl-9-tetradecenoic acid methyl ester, 12-methyl-9-tridecenoic acid methyl ester and 11-methyl-9-tetradecenoic acid methyl ester. The unique branched methyl ester mixture is reduced using standard procedures with copper chromite catalyst in the presence of hydrogen to give essentially a mixture of 12-methyltetradecan-1-ol, 12-methyltridecan-1-ol and 11-methyltetradecan-1-ol. The mixture is vacuum distilled to provide a purified mixture.

I.B. Sulfonation:

A reaction vessel that has agitation and a $N_2$ purge to exclude air is filled with 22.1 grams (approximately 0.1 mol) of the near terminal alcohol mixture prepared according to example I.A. 50 mls of diethyl ether is added. The mixture is chilled to −5° C. 12.23 grams (0.105 mol) of chlorosulfonic acid is added drop-wise while keeping the temperature of the mixture to below 10° C. Vacuum is applied to remove evolving HCl gas while the mixture was allowed to warm to ~30° C. Diethyl ether is replaced twice as it was evaporated while continuously mixing for two hours. Then the ether is removed by vacuum prior to the next step. The resulting mixture is added slowly, with mixing, to a stainless steel beaker containing 22.68 g of a 25% solution of sodium methoxide in methanol (0.105 mol) that is chilled in an ice bath. The mixture is stirred for an hour then poured into a stainless steel tray. The solvents are then evaporated and the sample further dried using a vacuum oven. A near-terminal branched alcohol sulfate surfactant is obtained.

I.C. Near Terminal Branched Alcohol Ethoxylate:

223.7 grams (1.0 mol) of the near terminal alcohol mixture of Example I.A. above plus sufficient catalyst to facilitate the reaction of the alcohol with ethylene oxide within a suitable period of time and in a controllable manner are charged to a 600 mL stainless steel stirred pressure vessel with a cooling coil. A suitable catalyst is 1.1 grams of a solution consisting of 50% potassium hydroxide in water. Other kinds and quantities of catalyst can be used. The reactor is heated while applying a vacuum for removing materials that can result in side products, such as water, that may be introduced with the catalyst, at a temperature that does not allow the loss of the near terminal alcohol mixture of example I.A., generally between 40° C. and 90° C., but preferably between about 60° C. and about at 80° C., when using a water aspirator as a vacuum source. The removal of water is facilitated by using low speed agitation, generally about 50 rpm, while sparging the mixture with a low level (trickle) stream of inert gas either through a bottom drain valve or through a stainless steel gas dispersion frit or any inert dip-tube or sintered metal fritted material or by sweeping the area above the mixture with inert gas. Samples can be drawn from the reactor and analyzed for water content using an appropriate analytical method such as Karl-Fischer titration. After completion of the water removal step, ethylene oxide can be added all at once if the reactor system is properly designed to prevent an uncontrolled rate of reaction. However, the best reaction control is obtained by first heating the reactor under a static vacuum (or optionally with added pressure from an inert gas such as $N_2$) to a temperature that is suitable for the reaction of the alcohol-catalyst mixture with ethylene oxide to occur with minimum side products and color generation, generally between 85° and 150° C., but preferably between about 110° C. and 130° C. Once the reactor has reached the desired temperature, 308 grams (7.0 mol) of ethylene oxide is added at a rate that will be controllable by the cooling system, generally over a period of 30 to 60 minutes. After the addition of ethylene oxide is completed, stirring and heating is continued until the ethylene oxide has been consumed by the reaction. The product can then be degassed and removed from the reaction vessel and stored as is or for long term storage the catalyst is neutralized with one equivalent of an acid selected from citric, HCl or sulfuric acid. The neutralized product can be filtered to remove any solid residue. The surfactant is now ready.

EXAMPLES

KEY: *=Derivable via metathesis of oleyl-based oil and 3-methyl-1-butene; *=sodium or ammonium salt; QSP=sufficient quantity for 100%; without units numbers are in wt %.

Cleansing Compositions (A to D)

| Component | A | B | C | D |
|---|---|---|---|---|
| 10-Methyldodecylsulfate[#] | 12 | 6 | — | — |
| 11-Methyldodecylsulfate[#]* | — | 6 | — | — |
| 10-Methyldodecylsulfate-ethoxylated[#] | — | — | 12 | 6 |
| 11-Methyldodecylsulfate-1-ethoxylated[#] | — | — | — | 6 |
| ocobetaine (CocoB) | 1-1.5 | 1-1.5 | 1-1.5 | 1-1.5 |
| Cationic polymer (e.g., AM:TRI, cationic guar gum) | 0.25 | 0.25 | 0.25 | 0.25 |
| Silicone | 1.0 | 1.0 | 1.0 | 1.0 |
| Ethylene glycol distearate (EGDS) | 1.25 | 1.25 | 1.25 | 1.25 |
| Sodium Lauryl Sulfate (SLS) | 1.5 | 1.5 | 1.5 | 1.5 |
| Finishing Agents (e.g., perfume, pH adjusters, water) | QSP | QSP | QSP | QSP |

Clarifying Cleansing Compositions (E to H)

| Component | E | F | G | H |
|---|---|---|---|---|
| 10-Methyldodecylsulfate[#] | 12 | 6 | — | — |
| 11-Methyldodecylsulfate[#]* | — | 6 | — | — |
| 10-Methyldodecylsulfate-ethoxylated[#] | — | — | 12 | 6 |
| 11-Methyldodecylsulfate-1-ethoxylated[#] | — | — | — | 6 |
| Cocobetaine (CocoB) | 1-1.5 | 1-1.5 | 1-1.5 | 1-1.5 |
| Sodium Lauryl Sulfate (SLS) | 2 | 2 | 2 | 2 |
| Cationic polymer (e.g., AM:TRI, cationic guar gum) | 0.25 | 0.25 | 0.25 | 0.25 |
| Other (e.g., perfume, pH adjusters, water) | QSP | QSP | QSP | QSP |

Compact Cleansing Compositions (J to N)

| Formulation/Component | I | J | K | L | M | N |
|---|---|---|---|---|---|---|
| 10-Methyldodecylsulfate[#] | 6 | 3 | — | — | — | — |
| 11-Methyldodecylsulfate[#] | — | 3 | 6 | — | — | — |
| 10-Methyldodecylsulfate-1-ethoxylated[#] | — | — | — | 20 | 10 | — |
| 11-Methyldodecylsulfate-1-ethoxylated[#] | — | — | — | — | 10 | 20 |
| Sodium Lauryl Sulfate (SLS) | 1.5 | 1.5 | 1.5 | 1.5 | 1.5 | 1.5 |
| Sodium Laureth Sulfate, 1-ethoxylated (SLE(1)S) | 16 | 16 | 16 | 0 | 0 | 0 |
| Cocobetaine (CocoB) | 1.9 | 1.9 | 1.9 | 1.9 | 1.9 | 1.9 |
| Cationic polymer (e.g., AM:TRI, cationic guar gum) | 0.1 | 0.1 | 0.1 | 0.1 | 0.1 | 0.1 |
| Large particle (LP)-Silicone (particles 30 microns) | 2.5 | 2.5 | 2.5 | 2.5 | 2.5 | 2.5 |
| Perfume | 1.5 | 1.5 | 1.5 | 1.5 | 1.5 | 1.5 |
| Ethylene glycol distearate (EGDS) | 1.25 | 1.25 | 1.25 | 1.25 | 1.25 | 1.25 |
| Other (e.g., perfume, pH adjusters, water) | QSP | QSP | QSP | QSP | QSP | QSP |

Silicone, SLS, and EGDS may be removed from any of compositions A-F to result in a clarifying shampoo.

Comparative Data
See key above.

| Formulation/Component | A | B | Control (C) |
|---|---|---|---|
| 10-Methyldodecylsulfate[#] | 6 | 3 | — |
| 11-Methyldodecylsulfate[#] | — | 3 | — |
| Sodium Lauryl Sulfate (SLS) | 1.5 | 1.5 | 7.5 |
| Sodium Laureth Sulfate, 1-ethoxylated (SLE(1)S) | 16 | 16 | 16 |
| Cocobetaine (CocoB) | 2 | 2 | 2 |
| Cationic polymer (e.g., AM:TRI, cationic guar gum) | 0.2 | 0.2 | 0.2 |
| Large particle (LP)-Silicone (particles 30 microns) | 2.5 | 2.5 | 2.5 |
| Perfume | 1.5 | 1.5 | 1.5 |
| Ethylene glycol distearate (EGDS) | 1.5 | 1.5 | 1.5 |
| Other (e.g., perfume, pH adjusters, water) | To 100 | To 100 | To 100 |
| Technical Measurements: Critical Micelle | | | |
| Concentration (ppm) | 147 ppm | 152 ppm | 82 ppm |
| Measured Performance | | | |
| Dissolution time (Dissolution Time Experiment) | 150 sec | 160 sec | 320 sec |
| Lathering time (Lathering Time Experiment) | 20 sec | 20 sec | 40 sec |
| Rinsing (gram water required per gram of hair [dry weight]) from Rinsing Experiment | 180 g | 200 g | 400 g |

Dissolution Time Experiment: 0.5 gram of composition (comprising 0.13 g total surfactant) is placed on a standard glass slide (Corning 2947 MicroSlides). The composition covered slide is allowed equilibrate for 1 minute at ambient conditions. The glass slide containing product is then suspended in a beaker containing 1 L of water (maintained @ 34° C.+/−2° C.). The solution is reproducibly stirred at 400 rpm (IKA BigSquid 1500 RPM Stirrer). A conductivity probe is inserted into the solution. The conductivity of the solution rises as the product dissolves. The time is then recorded from when the slide is placed into the water until the conductivity measure remains constant (product completely dissolved). Results are given as sec to dissolve.

Lathering Time Experiment (using controlled SITA method): The switch lather test method is designed to evaluate the lather ease and volume for compositions. Switches of Oriental virgin hair, flat construction, 15 g/10 inches, are treated uniformly with 0.1 g of artificial sebum from hexane solution to provide a realistic soil level. In the lather evaluation the switch is first wetted with tap water (100° F., 7-10 gpg hardness) and deliquored to a water content of 1 g H₂O per gram of hair (dray weight). 0.75 gram of composition (comprising 0.19 gram total surfactant) is applied to the center of the switch; the lower portion of the switch is then rubbed over the composition on the hair with 5 strokes in circular motion to distribute the composition evenly. This is followed by 40 strokes with a back and forth motion. Lather ease is determined by the time (sec) required for lather volumes to reach consumer relevant levels (200 mL of lather).

Rinsing Experiment (friction on hair measured as hair is rinsed at controlled rate): Four gram, 8 inch length hair switches are combined in a hair switch holder, wetted for ten sec with manipulation with water at 40° C. and typical hardness (9-10 gpg) to ensure complete and even wetting. Composition is applied uniformly over the length of the combined switches from one inch below the holder towards the end at a level of 0.1 gram composition (comprising 0.026 gram total surfactant) per one gram of dry hair (0.1 gram per gram hair, or 2 gram for 20 gram of hair). For more concentrated prototypes the usage level is reduced to 0.05 gram per gram of hair (0.013 g total surfactant). The switch combo is lathered by a rubbing motion typical of that used by consumers for 30 sec and rinsed with water flowing at 1.5 gal/min at 40° C. (with the hair being manipulated) to insure completeness for 30 sec. Rinsing then begins as the friction of the hair is measured via Load Cell instrument such as Instron or TA-XT. During the rinsing, the water flow rate is controlled as above and strokes of the Load Cell instrument show increasing friction as the shampoo is removed from the hair. Compositions that more quickly get to consumer relevant frictions denoting the composition is completely rinsed (1000 gram of force) require less water. The results are reported as gram of water required to reach this friction. From FIG. 1, the calculation was based on the following measurements: each stroke is 12 sec, and the water flow rate is 400 mL/min A consumer relevant friction point representing end of rinse of composition from the hair (here 1000 g force), the number of strokes needed to reach this force can be found and the amount of water employed after this number of strokes calculated. For example, 10 strokes means 120 sec means 800 gram of water. The switches weight 4 gram. 800 gram of water becomes 200 gram of water/gram of hair.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

What is claimed is:

1. Method of cleansing hair comprising:
(a) applying a composition to the hair;
(b) dissolving and lathering the composition using a water-based solvent;
(c) rinsing the hair with a water-based solvent;
wherein during the rinsing a total of about 100 gram to about 300 gram of water-based solvent per gram of hair (dry weight) is employed;
wherein the composition comprises from about 3 wt % to about 35 wt % of a mixture of at least two compounds of Formula I:

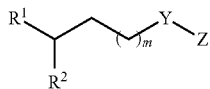

wherein $R^1$ is methyl group, $R^2$ is hydrogen or methyl group and m is 6 to 14; Y is null, or $W_p$; W is selected from the group consisting of ethylenoxy, propylenoxy, butylenoxy, and mixtures thereof; p is 1 to 30; Z is a hydrophilic moiety selected from the group consisting of hydroxy, carboxylate, sulfate, disulfate, sulfonate, disulfonate, glycerol ester sulfonate, amine, monoalkylamine, dialkylamine, amine oxide, a polyhydroxy moiety, a phosphate ester, glycerol sulfonate, polygluconate, a polyphosphate ester, phosphonate, sulfosuccinate, sulfosuccaminate, glucamide, taurinate, sarcosinate, glycinate, isethionate, dialkanolamide, monoalkanolamide, monoalkanolamide sulfate, diglycolamide, diglycolamide sulfate, a glycerol ester, a glycerol ester sulfate, a glycerol ether, a glycerol ether sulfate, a polyglycerol ether, a polyglycerol ether sulfate, sorbitan ester, an alkylpolyglucoside, urea, ammonioalkanesulfonate, amidopropyl betaine, an allylated quat, an alkyated/polyhydroxyalkylated quat, an alkylated quat, an alkylated/polyhydroxylated oxypropyl quat, a glycerol ester quat, a glycol amine quat, imidazoline, alken-2-yl-succinate, a sulfonated alkyl ester, and a sulfonated fatty acid wherein, in at least one of the compounds of Formula I, $R^1$ and $R^2$ are both methyl groups;

wherein the composition comprises less than about 0.5 wt % polyacrylate associative thickeners and trihydroxystearin polymeric thickeners.

2. Method according to claim 1, wherein during the rinsing a total of about 120 gram to about 270 gram of water-based solvent per gram of hair (dry weight) is employed.

3. Method according to claim 1, wherein during the rinsing a total of about 170 gram to about 210 gram of water-based solvent per gram of hair (dry weight) is employed.

4. Method according to claim 1, wherein the weight ratio of linear compound to branched compound (linear:branched) is from about 10:1 to about 1:2.

5. Method according to claim 1, wherein the weight ratio of linear compound to branched compound (linear:branched) is from about 4.5:1 to about 1.75:1.

6. Method according to claim 1, wherein the composition further comprises a cosmetically acceptable aqueous carrier and is in the form of a pourable liquid.

7. Method according to claim 1, wherein the composition comprises from about 10 wt % to about 20 wt % of a mixture of at least two compounds of Formula I.

8. Method according to claim 1, wherein dissolving comprises a dissolution time of from about 0.1 sec to about 300 sec.

9. Method according to claim 1, wherein dissolving comprises a dissolution time of from about 120 sec to about 180 sec.

10. Method according to claim 1, wherein the lathering comprises a lathering time of from about 0.1 sec to about 80 sec, in order for a composition comprising 0.19 gram total surfactant to reach 200 mL total volume of lather.

11. Method according to claim 1, wherein the lathering comprises a lathering time of from about 5 sec to about 50 sec, in order for a composition comprising 0.19 gram total surfactant to reach 200 mL total volume of lather.

12. Method according to claim 1, where the composition further comprises a cationic surfactant, and wherein the cationic surfactant is selected from the group consisting of: behenyl trimethyl ammonium chloride, behenyl trimethyl ammonium methyl sulfate behenyl trimethyl ammonium ethyl sulfate, stearyl trimethyl ammonium chloride, stearyl trimethyl ammonium methyl sulfate and stearyl trimethyl ammonium ethyl sulfate.

13. Method according to claim 1, wherein the linear compound is the salt of an anionic surfactant comprising 12 to 14 carbon atoms.

14. A composition for cleansing hair wherein the composition dissolves in a water-based solvent with a dissolution time of from about 0.1 sec to about 300 sec, wherein the composition comprises from about 3 wt % to about 20 wt % of a mixture of at least two compounds of Formula I as described in claim 1.

* * * * *